United States Patent [19]

Harding

[11] Patent Number: 4,896,342

[45] Date of Patent: Jan. 23, 1990

[54] X-RAY APPARATUS

[75] Inventor: Geoffrey Harding, Hamburg, Fed. Rep. of Germany

[73] Assignee: U.S. Philips Corporation, New York, N.Y.

[21] Appl. No.: 173,693

[22] Filed: Mar. 25, 1988

[30] Foreign Application Priority Data

Apr. 1, 1987 [DE] Fed. Rep. of Germany ....... 3710936

[51] Int. Cl.$^4$ .......................................... G01N 23/201
[52] U.S. Cl. ......................................... 378/87; 378/86
[58] Field of Search ............................ 378/86, 87, 146

[56] References Cited

U.S. PATENT DOCUMENTS

| | | | |
|---|---|---|---|
| 3,936,638 | 2/1976 | Gibbons | 378/87 |
| 3,961,186 | 6/1976 | Leunbach | 378/86 |
| 3,965,353 | 6/1976 | Macovski | 378/87 |
| 4,653,083 | 3/1987 | Rossi | 378/197 |
| 4,716,581 | 12/1987 | Barnd | 378/197 |

FOREIGN PATENT DOCUMENTS 2075370 4/1987 Japan ..................................... 378/87

Primary Examiner—Janice A. Howell
Assistant Examiner—John C. Freeman
Attorney, Agent, or Firm—Jack E. Haken

[57] ABSTRACT

The invention relates to an X-ray apparatus, comprising an essentially monochromatic radiation source which irradiates an examination zone in different positions by means of a primary beam having a small cross-section, a first position-sensitive detector device which measures, on the other side of the examination zone, the radiation elastically scattered in the primary beam, and means for reconstructing an image of the irradiated cross-section. Assignment of an X-ray quantum is realized in that the first detector device is constructed so that it measures essentially the energy loss of the X-ray quanta incurred therein due to Compton scattering, there also being provided a second position-sensitive detector device, and a coincidence device which determines the coincidence of the signals of the two detector devices, the reconstruction means being constructed so that, in the case of coincidence of the detector output signals, the path of the X-ray quantum causing these signals is determined and therefrom, and from the energy loss measured in the first detector device, the position of the scatter point on the primary beam is determined.

6 Claims, 2 Drawing Sheets

X-RAY APPARATUS

The invention relates to an X-ray apparatus comprising a substantially monochromatic radiation source which irradiates an examination zone in different positions by means of a primary beam having a small cross-section, a first position-sensitive detector device which measures, on the other side of the examination zone, the radiation elastically scattered in the primary beam, and means for reconstructing an image of the irradiated cross-section.

An X-ray apparatus of this kind is known from DE-OS 34.06.905 and DE-OS 35.26.015. Such apparatus utilizes the fact that, in a small scatter angle range (up to approximately 12°), the elastically scattered radiation (which, as opposed to Compton scattering, does not incur an energy loss during the scattering process), exhibits a scatter angle dependency which is characteristic of the material in which scattering takes place. Therefore, for different angles within this angular range or for different momentum transfers cross-sectional images can be formed of the scatter density distribution in the examination zone. Generally, these images are suitable distinct from one another and offer information as regards the material in the cross-section.

The detector output signal is then determined by the path integral over the scatter density along the path followed by the primary beam through the examination zone. Consequently, a detector signal cannot be directly assigned to a given point or a given part of the path, not even when scattering takes place exclusively in the relevant point or the relevant part. However, from position emission tomography it is known that improved reconstruction is possible (with a better signal-to-noise ratio) if the origin of a quantum can be more accurately localized (see J. Com. Ass. Tomography, 1981, page 227).

Therefore, it is an object of the invention to construct an apparatus of the kind set forth so that it is suitable for determining at least approximately the position wherefrom a given X-ray quantum is scattered to a detector.

This object is achieved in accordance with the invention in that the first detector device is constructed so that it measures essentially the energy loss of the X-ray quanta which occurs therein due to Compton scattering, there being provided a positive-sensitive detector device and a coincidence device which determines the coincidence of the signals of the two detector devices, the reconstruction means being constructed so that, in the case of coincidence of the detector output signals, the path of the X-ray quantum causing these signals is determined and therefrom, and from the energy loss measured in the first detector device, the position of the scatter point on the primary beam is determined.

The invention is based on the following considerations: an X-ray quantum which is elastically scattered in the primary beam and which is subjected to a Compton scattering process in the first detector device and subsequently reaches the second detector device generally is detected substantially simultaneously by both detector devices. Therefore, when the coincidence device detects the coincidence of two output signals of the two detector devices, it may be assumed that they relate to the same X-ray quantum.

In both position-sensitive detector devices a given location of incidence can be assigned to the X-ray quantum; the connecting line between the two locations of incidence represents the path followed by the X-ray quantum from the first to the second detector device. From the energy loss incurred by the X-ray quantum due to Compton scattering in the first detector device in which it is also measured, the scatter angle wherethrough the X-ray quantum is deflected from its previous direction due to the Compton scattering can be determined for a given energy of the X-ray quanta in the primary beam. Therefore, the X-ray qauntum must have originated from a point on the envelope of a cone whose angle of aperture equal twice the scatter angle, whose apex is situated in the location of incidence of the X-ray quantum in the first detector device, and whose axis is given by the connecting line between the locations of incidence of the X-ray quantum in the two detector devices. Because it is also known that the X-ray quantum originates from the primary beam, the point of origin of the X-ray quantum will be given by the point of intersection of the primary beam with said cone envelope.

It is to be noted that from Med. Phys., Vol. 10, No. 4, July/August 1983, pp. 421 ff a device is known which comprises a first detector device and a second detector device and in which the envelope of cone wherefrom the quantum must have originated is also determined from the energy loss in the first detector, however, this concerns a device for emission computer tomography for reconstructing only the distribution of a radionuclide in the human body.

The invention will be described in detail hereinafter with reference to the drawings. Therein:

Figure 1:
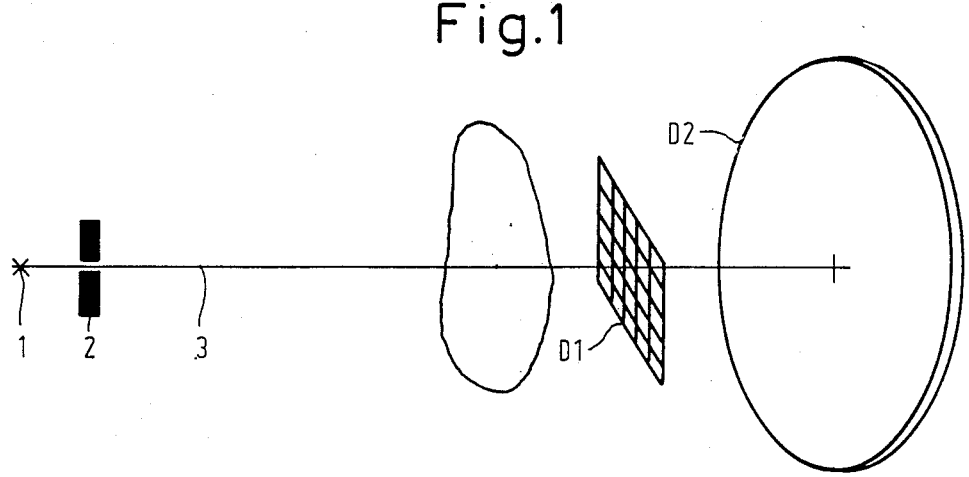
FIG. 1 shows diagrammatically an X-ray apparatus in accordance with the invention.

The reference numeral 1 in FIG. 1 denotes a radiation source which generates essentially monochromatic radiation. A radiation source of this kind only generates radiation having a given energy or in a comparatively narrow range around this energy and can be manufactured in various ways. One possibility consists in the use of a radionuclide. Another possibility consists in the use of X-ray fluorescence and a third possibility consists in the extraction of a narrow energy range from the spectrum of an X-ray source by means of absorption band-edge filters.

A diaphragm device 2 which is arranged in the beam path ensures that only a primary beam 3 having a narrow cross-section (pencil beam) irradiates an object 4 to be examined. Behind the examination zone there is arranged a first detector device D1 which detects on the one hand the intensity of the primary beam and on the other hand also the intensity of the scattered radiation which is elastically scattered at small angles; this is known per se from German Patent Application P 35.26.015. Therebehind there is arranged a second detector D2 which detects the X-ray scattered in the first detector device.

The first detector device consist of a number of detector elements which are arranged in the form of a matrix or a checkerboard, for example, 10×10 detector elements. The energy of the primary radiation and the material of these detector elements are adapted to one another so that the attenuation of the X-rays is caused essentially by Compton scattering and only to a minor degree by photo absorption. The amplitude of the output signal of each detector elements is proportional to the energy loss incurred by the X-ray quanta due to Compton scattering. It may also occur that X-ray quanta are elastically scattered in the detector device D1, but they cannot be detected by means of the device D1 because no energy loss is incurred. Suitable detector elements consist of a lithium-doped silicon layer having a thickness of approximately 10 mm. In a detector element of this kind approximately ⅓ of the X-ray quanta is scattered when the energy of the X-ray quanta in the primary beam is 60 KeV, and only a small part is absorbed by photoabsorption.

The second detector D2 is formed by a gamma camera which is concentrically arranged with respect to the primary beam 3 at a distance of approximately 10 cm from the detector D1, the detection surface area of said gamma camera being so large that essentially all X-ray quanta scattered in the detector D1 up to scatter angles of 90° are absorbed therein. As is known, in addition to a signal which depends on the energy of a gamma or X-ray quantum, a camera of this kind also supplies further signals which are dependent on the point of incidence of the gamma quantum on the entrance face of the gamma camera. The energy resolution of such a gamma camera can be used for reducing interference radiation. This is because, when the energy of the gamma quanta in the primary beam of 60 keV, the energy of the Compton-scattered gamma quanta must be between approximately 50 and 60 keV. Quanta having a substantially lower or higher energy cannot originate from the primary beam; therefore, the associated output signals are suppressed.

Figure 2:
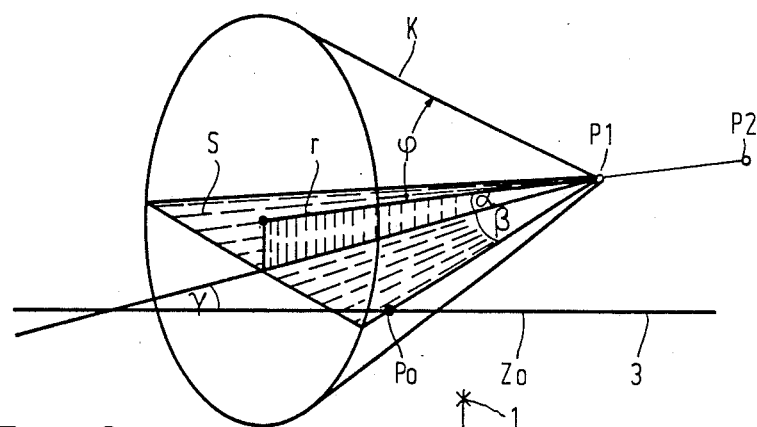
FIG. 2 illustrates the geometrical relationships in such an X-ray apparatus.

FIG. 2 illustrates the determination of the point Po on the primary beam 3 in which a gamma quantum is elastically scattered in a device as shown in FIG. 1. P1 is the point on the first detector device D1 in which the elastically scattered X-ray quantum is incident, and P2 denotes the point on the second detector device D2 in which the X-ray quantum scattered by Compton scattering from the point P1 is incident. The connecting line between the points P1 and P2 corresponds to the path of the X-ray quantum between the detectors. Extension of this connection beyond the point P1 results in a straight line r which is generally not situated in the same plane as the primary beam. From the energy loss of dE of the X-ray quantum, measured by detector device D1, there can be calculated the scatter angle Φ wherethrough the elastically scattered X-ray quantum is deflected from is previous path during the Compton scatterng process in the point P1. This is subject to the following equation:

$$\Phi = \text{arc cos} (1 - Eo1/(E-dE) - 1/E)) \quad (1)$$

Therein, arc cos is the inverse function of the cosine function (cos (arc cos x)=x), Eo is the steady state energy of an electron (approximately 511 keV) and E is the energy of the X-ray quanta in the primary beam.

Each X-ray quantum which is scattered in the point P1 to the point P2 by a Compton scattering process, during which it is deflected out of its original direction through an angle Φ, must be situated on the envelope of a cone K whose apex is situated in the point P1, whose axis is given by the straight line r, and whose angle of aperture amounts to 2Φ. The point Po in which the primary beam 3 penetrates the envelope of the cone, therefore, is the point in which the X-ray quantum was elastically scattered to the point P1. The position of this point on the primary beam 3, i.e. its distance z0 from the plane of the first detector device D1, can be determined as follows. The plane which contains the primary beam 3 and the point P1 is intersected by the cone K; the plane of intersection S is shaded in FIG. 2. The plane of intersection is bounded by two generatrices, one of which intersects the primary beam 3 within the examination zone in the point Po. For determining the angle of intersection of this line with respect to the primary beam 3, first the straight line r which extends at the angle α with respect to the plane of intersection S is projected onto the plane of intersection, the projection line intersects the primary beam at an angle γ. It divides the plane of intersection S into two equal halves and encloses the angle β with respect to the two said generatrices. This can be calculated by means of the equation:

$$\beta = \text{arc tan} (\cos \alpha \sqrt{\tan^2\psi - \tan^2\alpha}) \quad (2)$$

Therein, arc tan is the inverse function of the tangent function (tan (arc tan x)=x). The distance z0 of the point Po from the plane of the detector device D1 can thus be calculated as:

$$z_0 = d/\tan(\beta+\gamma) \quad (3)$$

Therein, d is the distance between the point P1 and the primary beam 3.

As appears from the foregoing, each time the point on the primary beam 3 can be determined wherefrom the X-ray quantum is elastically scattered to the point P1. The associated scatter angle β+γ is generally comparatively small (smaller than approximately 12°). Therefore, and because the energy loss incurred by an X-ray quantum during Compton scattering can be determined only comparatively inaccurately (to approximately 200 eV by means of a contemporary detector), exact localization of the point of origin of the X-ray quantum is not possible and neither is exact determination of the scatter angle (β+γ) enclosed by the path of the elastically scattered X-ray quantum with respect to the primary beam. However, when the part of the primary beam which passes through the examination zone is divided into, for example, four parts or when the scatter angle range is subdivided into some sub-ranges, the X-ray quantum can be assigned to each time one of these parts or sub-ranges. The reconstruction is thus already improved substantially.

Figure 3:
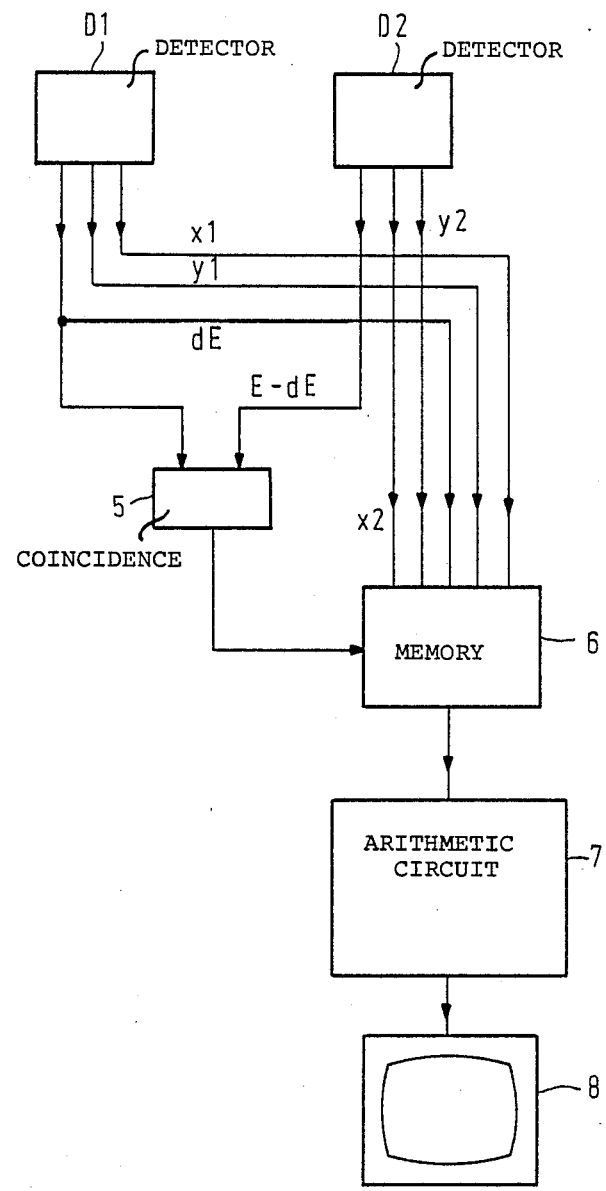
FIG. 3 shows a block diagram of a unit suitable for evaluating the detector output signals.

FIG. 3 shows a block diagram of a circuit which can be used in conjunction with the invention. The two detectors D1 and D2 supply signals which are proportional to the energy loss dE or to the energy E-dE remaining after the Compton scattering process. These signals are applied to a coincidence circuit 5. The two detector devices D1 and D2 also supply signals x1, y1 and x2, y2, respectively, which define the position of the point of incidence of the relevant X-ray quantum in a cartesian xy coordinat system whose origin coincides, for example with the primary beam 3. Together with the signal which is supplied by the detector D1 and which corresponds to the energy loss dE, these signals are applied to the input of a memory circuit 6. This circuit is controlled by the coincidence circuit so that the input values are stored only if the signals supplied by the detectors D1 and D2 appear simultaneously. An arithmetic circuit 7 calculates therefrom, in the manner described with reference to FIG. 2, the scatter angle Φ+γ or the point of origin Po of the X-ray quantum elastically scattered in the primary beam 3. Using the data thus obtained, the scatter density distribution is reconstructed for display on a display device 8.

Reconstruction can take place in the same way as described with reference to FIG. 3 of German Patent Application P 34.06.905; however, as from the beginning the values measured by the first detector device can be assigned to a given angular range or to a given part of the beam path. This reconstruction method is based on the assumption that the examination zone has been irradiated by the primary beam along a plurality of parallel beam paths and that the direction of the beam has been rotated through a small angle with respect to the examination zone and hence shifted again, etc. The reconstruction by means of the measurement values derived by means of this method produces images of the scatter density distribution for each time one scatter angle or scatter angle range, thus providing information as regards the composition of the examination zone.

Figure 4:
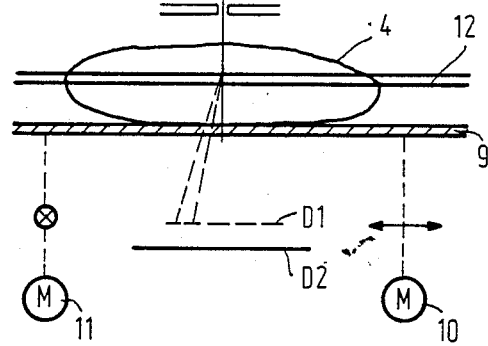
FIG. 4 shows a layer imaging apparatus constructed accordingly.

However, it is alternatively possible to extract the data required for the layer reconstruction by way of a scanning motion during which the examination zone is scanned by meander-like displacements perpendicularly to the primary beam. As appears from FIG. 4, a table 9 on which the patient 4 is situated can then be displaced laterally (horizontally and in the plane of drawing) by means of a first motor 10 and perpendicularly to the plane of drawing by means of a second motor 11. However, it is equally well possible to displace the device 1, 2, D1 and D2 in a meander-like fashion with respect to the stationary patient. Output signals of the detector device D1 which are associated with the same scatter angle and which are originate from detector elements which are situated at approximately the same distance from the primary beam must then originate from the same layer 12 of the patient. As is denoted by broken lines in FIG. 4, detector elements which are situated further from the primary beam 3 intercept the scatter radiation from the same layer at a larger scattered angle. The scatter density distribution in a layer 12 (perpendicular to the plane of drawing of FIG. 4) can thus be reconstructed, that is to say for different scatter angles, without it being necessary to rotate the primary beam 3 with respect to the patient 4.

In the method in accordance with the invention not every X-ray quantum in the first detector 1 is scattered by a Compton process; however, photoabsorption takes place either in the first or the second detector. The signals produced thereby in the detectors can be additionally taken into account used for image reconstruction in known manner (see DE-OS 34.06.905 and 35.26.015).

What is claimed is:
1. In an X-ray apparatus of the type comprising: a radiation source (1) which irradiates a cross-section of an examination zone (4) by means of a primary beam of substantially monochromatic radiation wherein said primary beam interacts with said cross section of said examination zone to produce elastically scattered X-ray quanta from the examination zone, said primary beam having a small cross-section, first position-sensitive detector means (D1) which measure X-ray quanta elastically scattered in the primary beam within the examination zone, and means (6, 7) for reconstructing an image of the irradiated cross-section of the examination zone, wherein, as an improvement the first position-sensitive detector means (D1) measures the energy loss of the X-ray quanta which occurs in said first position-sensitive detector means due to Compton scattering, and further comprising second position-sensitive detector means (D2), and coincidence means (5) which determine the coincidence of signals from the first and second position-sensitive detector means (D1, D2), the reconstruction means (6, 7) functioning so that, in the case of said coincidence of detector means output signals, a path (r) of an X-ray quantum causing said signals is determined, and from said determination of the path and the energy loss (dE) measured in the first detector means, the position (zo) of a scatter point on the primary beam (3) is determined.

2. An X-ray apparatus as claimed in claim 1, further comprising means (10, 11) for generating a relative motion of the primary beam with respect to the examination zone in two directions which are perpendicular to one another and perpendicular to the direction of the primary beam.

3. A device as claimed in claim 1, further comprising means for rotary and translatory displacement of the primary beam (3) with respect to the examination zone.

4. A device as claimed in any one of the preceding claims, characterized in that the second position-sensitive detector means (D2) is a gamma camera.

5. An X-ray apparatus as claimed in claim 1 wherein the first position-sensitive detector means comprises a matrix of semiconductor detector elements.

6. An X-ray apparatus claimed in claim 5, wherein the semi-conductor detector elements are lithium-doped silicon detectors.

* * * * *